United States Patent [19]
Abdel-Rahman

[11] Patent Number: 5,035,138
[45] Date of Patent: Jul. 30, 1991

[54] MASS FLOW SENSOR HAVING WIDE DYNAMIC RANGE

[75] Inventor: Mahmoud F. Abdel-Rahman, West Grove, Pa.

[73] Assignee: Hewlett-Packard Company, Palo Alto, Calif.

[21] Appl. No.: 512,857

[22] Filed: Apr. 23, 1990

[51] Int. Cl.$^5$ .............................................. G01F 1/68
[52] U.S. Cl. .............................. 73/204.15; 73/204.25
[58] Field of Search ........... 73/204.12, 204.15, 204.24, 73/204.25, 204.27

[56] References Cited

U.S. PATENT DOCUMENTS

| | | | |
|---|---|---|---|
| 3,229,522 | 1/1966 | Benson | 73/204.12 |
| 3,246,523 | 4/1966 | Richard | 73/204.25 |
| 4,107,991 | 8/1978 | Benson | 73/204.25 |

*Primary Examiner*—Herbert Goldstein
*Attorney, Agent, or Firm*—Richard Schuette

[57] ABSTRACT

A method and apparatus for sensing the mass flow of a fluid and for generating an output signal representative of the sensed mass flow are shown to include a conduit formed from resistive material, a voltage source connected to a first point on the conduit, for providing a voltage to the first point in response to a control signal, a differential amplifier wherein the output of the amplifier is representative of the difference in voltage between a second point on the conduit and a third point on the conduit, and a controller for generating the control signal so that the voltage provided to the first point is regulated in relation to the flow of fluid through the conduit. In an especially preferred embodiment the resistive material is Nickel-52. In a further embodiment, the controller generates the control signal so that the voltage applied to the first point is regulated to maintain the average resistance of the conduit at a desired value. In one embodiment, the desired value is a constant value. In another embodiment, the controller generates the control signal so that the voltage applied to the first point is maintained at a desired value. In this last embodiment, it is preferred to compensate the output signal to account for the cooling of the conduit as the fluid passes therethrough.

24 Claims, 2 Drawing Sheets

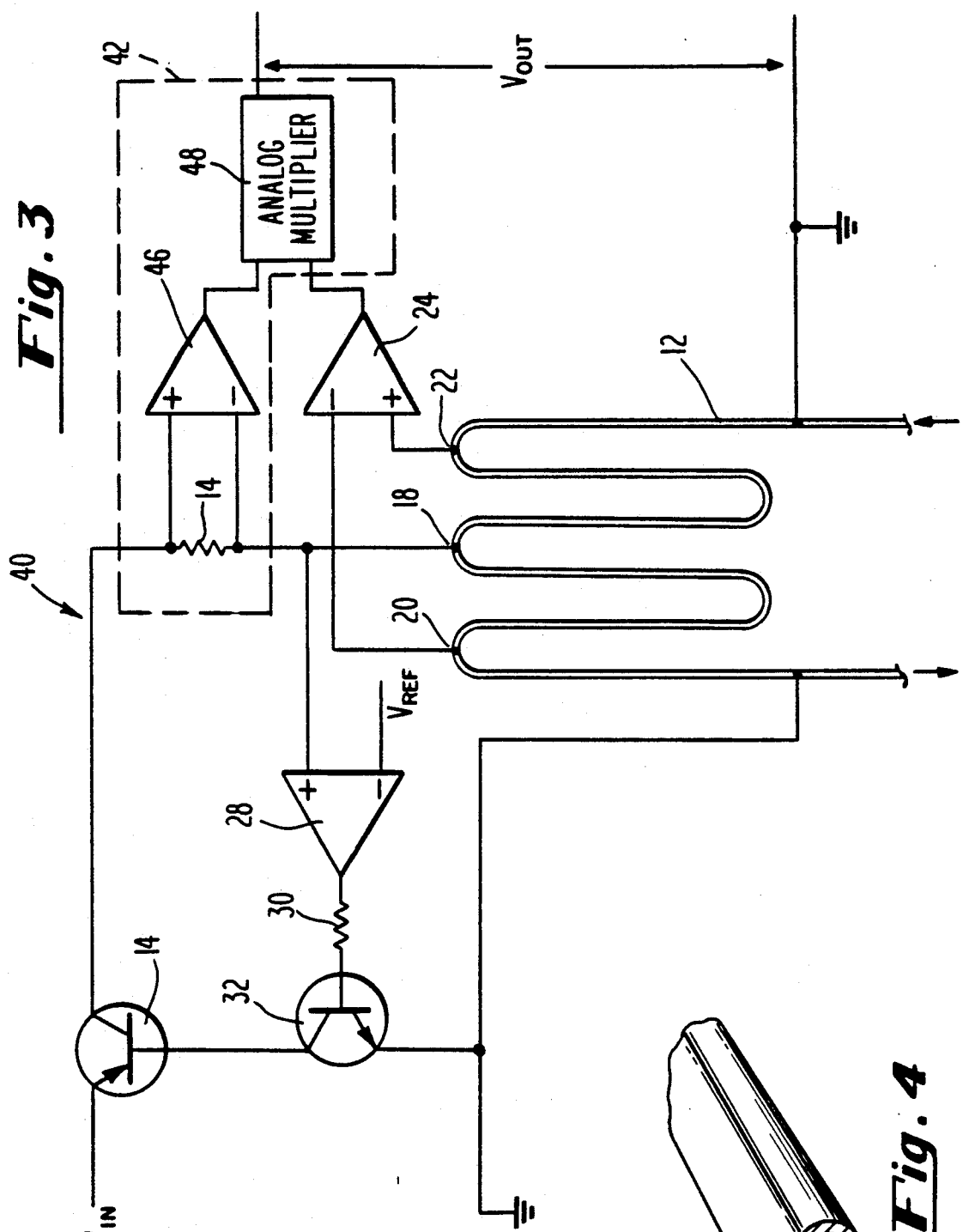

MASS FLOW SENSOR HAVING WIDE DYNAMIC RANGE

FIELD OF THE INVENTION

The present invention relates to the field of mass flow sensors, particularly methods and apparatus for maximizing the dynamic range of mass flow sensors.

BACKGROUND OF THE INVENTION

In analytical chemistry, liquid and gas chromatography techniques, as well as supercritical fluid chromatography techniques, have become important tools in the identification of chemical sample components. The basic principal underlying all chromatographic techniques is the separation of the sample chemical mixture into individual components by transporting the mixture in a moving fluid through a porous retentive media. The moving fluid is referred to as the mobile phase and the retentive media has been referred to as the stationary phase. Generally, such techniques require the analyst to monitor and/or control the mass-flow of the mobile phase. Such monitor or control operation, typically involves measuring the mass flow of a particular fluid in the chromatographic system. To this end, several mass-flow sensing devices have been developed.

One type of mass-flow sensor which has been developed for use with Tylan Mass-Flow Meters is said to include two heated resistance thermometers mounted on a small, stainless-steel sensor tube in spaced relationship to one another. It has been stated that when gas is flowing through the tube, heat is transferred by the moving fluid to the downstream thermometer thereby producing a signal proportional to the gas flow. Each resistance thermometer forms a part of a bridge and amplifier circuit that produces a 0 to 5 volts direct current (DC) signal proportional to the gas. See promotional literature for Tylan Mass-Flow Meters, page 1.

A similar type of mass-flow sensor is disclosed in Brooks Mass-Flow Meter descriptive literature by Brooks Instrument Division, Emerson Electric Company, 1981. The operation of the mass-flow sensor is stated as initially directing regulated heat to the midpoint of a flow-carrying sensor tube. Resistance temperature measuring sensors are stated to be positioned at equal distance points upstream and downstream of the heater. When gas is flowing through the sensor tube, the gas stream is said to carry heat from the upstream sensor to the downstream sensor. An increasing temperature difference developing between the two sensors is said to be proportional to the amount of gas flowing through the sensor. It is indicated that the temperature difference is interpreted by a bridge circuit and an amplifier provides a 0-5 volt DC output to an indicator and/or controller. Other devices of this type are described in Gallant, J., Thermal Mass-flow Transducers, Sensors Offer Fast Response Times, Electronic Design News, May 25, 1989, pages 55-68.

The problem with the above-described sensors is their limited dynamic range. Typically sensors are rated for a range of flow-rates, for example one sensor might be rated for the range from 0 to 100 mL per minute while another sensor may be rated from 0 to 10 mL per minute. The reason for this rating is that such previous sensors are subject to saturation. Saturation occurs when the flow of fluid through the mass-flow sensor is such that the heat exchange time constant between the sensor and the fluid is exceeded. In other words, as fluid moves faster and faster through the sensor, a point is reached where less rather than more differential heat is transferred to the downstream and upstream temperature sensors. This results in a decrease in the temperature difference between the sensors. While such a decrease in differential temperature is normally indicative of a decrease in mass-flow, in fact, mass-flow is increasing.

Consequently, a need exists for a mass-flow sensor having a wide dynamic range so that a single sensor could be used in multiple applications as compared to previously dedicated sensors for particular application mass flow ranges.

The present invention overcomes the problems of the past and provides a mass-flow sensor having a wide dynamic range of operation, in part, by providing a sensor element which in one embodiment is controlled in order to maintain a constant average resistance, while the temperature and resistance widely varies across the sensor element. In that embodiment, the difference in resistance between the first and second halves of the sensor element is a measure of mass flow.

It will be noted that U.S. Pat. No. 4,449,401 Kaiser, et al. discloses the use of a heated sensor 108. It is stated that the current through the sensor is adjusted to keep the temperature, and thus resistance at a single location in the mass-flow, constant. The current required to maintain constant resistance is said to be directly related to massflow. In order to determine mass-flow, a matched sensor used to determine ambient temperature is required. The differences between the device of Kaiser, et al. and the present invention will be appreciated from the following description.

SUMMARY OF THE INVENTION

The advantages of the invention are achieved in a method and apparatus for sensing the mass flow of a fluid and for generating an output signal representative of the sensed mass flow are shown to include a conduit formed from resistive material, a voltage source connected to a first point on the conduit, for providing a voltage to the first point in response to a control signal, a differential amplifier wherein the output of the amplifier is representative of the difference in voltage between a second point on the conduit and a third point on the conduit, and a controller for generating the control signal so that the voltage provided to the first point is regulated in relation to the flow of fluid through the conduit. In an especially preferred embodiment the resistive material is Nickel-52. In a further embodiment, the controller generates the control signal so that the voltage applied to the first point is regulated to maintain the resistance of the resistive material at a desired value. In one embodiment, the desired value is a constant value. In another embodiment, the controller generates the control signal so that the voltage applied to the first point is maintained at a desired value. In this last embodiment, it is preferred to compensate the output signal to account for the cooling of the conduit as the fluid passes therethrough.

BRIEF DESCRIPTION OF THE DRAWINGS

The present invention will be better understood, and its numerous objects and advantages will become apparent by reference to the following detailed description of the invention when taken in conjunction with the following drawings, in which:

FIG. 3 is a schematic diagram of an alternate embodiment of the present invention; and FIG. 4 is an alternate embodiment of the section view shown in FIG. 2.

DETAILED DESCRIPTION OF THE PREFERRED EMBODIMENT

Figure 1:
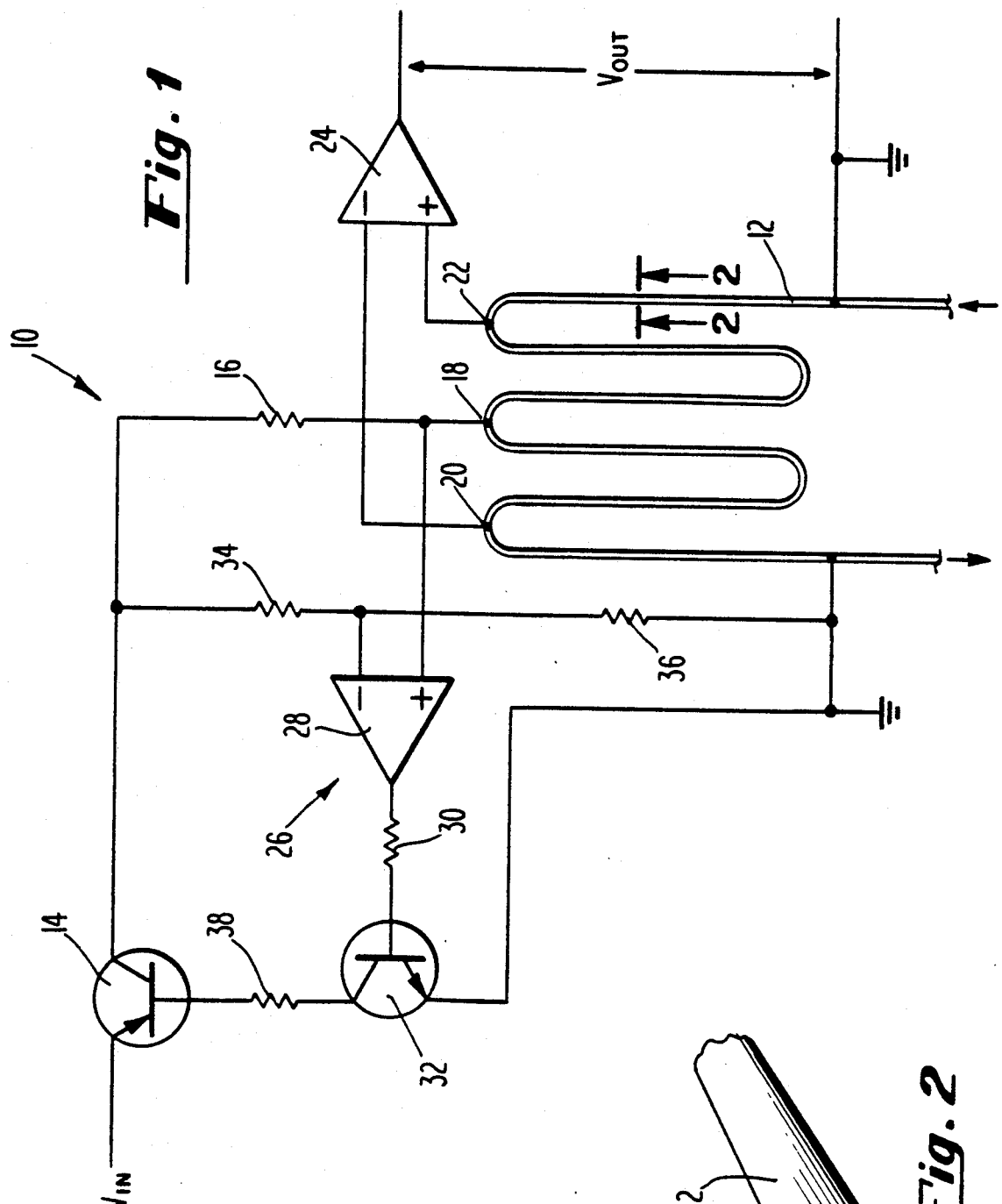
FIG. 1 is a schematic diagram of one embodiment of the mass flow sensor of the present invention.
Figure 2:
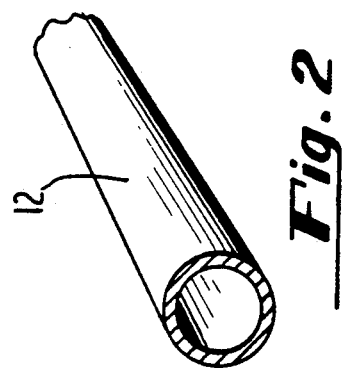
FIG. 2 is a perspective section view along the line 2—2 of FIG. 1.

A new and novel mass flow sensor is shown in FIG. 1 and is generally designated 10. Sensor 10 senses the massflow of a fluid flowing through conduit 12 and generates an output signal representative of such massflow. Conduit 12 is formed from resistive material and, as shown in FIG. 2, is generally cylindrical in shape. In the preferred embodiment, conduit 12 is formed from CARPENTER GLASS SEALING "52" (Nickel-52) sold by the Carpenter Technology Corporation. Nickel-52 is a 50.50% nickel-iron alloy and is stated to include carbon 0.01%, manganese 0.3%, silicon 0.2%, nickel 50.50% and the balance being iron. Nickel-52 is preferred because of its high electrical resistivity (430 microhms-mm) and high temperature coefficient of resistance (0.0029 per ° C.)

A voltage source, consisting of transistor 14 and resistor 16 provide a voltage to a first point 18 on conduit 12 in response to a control signal. When voltage is applied at point 18, voltage will also appear at second point 20 and third point 22 on conduit 12. A differential amplifier 24 is connected to determine the difference in voltage between points 20 and 22 and to generate an output signal ($V_{out}$). When no fluid is flowing through conduit 12 and assuming relative uniformity of resistance in conduit 12, identical voltages will be present at points 20 and 22. Since the voltages are virtually identical, the output of differential amplifier 24 will be 0, indicating no mass flow.

A controller 26 is shown to include differential amplifier 28, resistor 30 and transistor 32. The negative input to differential amplifier 28 is a voltage resulting from the divider circuit arrangement including resistors 34 and 36. As such, the voltage provided to the negative input of differential amplifier 28 is proportional to the voltage provided by the voltage source, i.e. transistor 14. The positive input of differential amplifier 28 is connected to point 18 on conduit 12. The output of differential amplifier 28 provides more or less bias to the base of transistor 32, which in turn provides more or less bias through resistor 38 to the base of transistor 14. In other words, the output of differential amplifier 28 controls the voltage provided by transistor 14 to point 18. As will be seen, such voltage is controlled in relation to the flow of fluid through conduit 12.

As shown in FIG. 1, point 18 exists at the mid-point of conduit 12 and lies between points 20 and 22. As will also be appreciated from FIG. 1, points 20 and 22 are spaced equidistant from point 18.

In operation, controller 26 generates the control signal for regulating the voltage transmitted through transistor 14 to point 18 in order to maintain the average resistance of conduit 12 at a desired value. It will be recalled that as the temperature of conduit 12 changes, its resistance value changes. In the embodiment depicted in FIG. 1, the average resistance value of conduit 12 is maintained at a constant value. This result is achieved by regulating the amount of voltage applied to point 18. The positive input of differential amplifier 28 is a voltage resulting from the divider circuit arrangement of resistor 16 and the resistance of conduit 12 between point 18 and ground. The portions of conduit 12 between point 18 and ground which include points 20 and 22 will be referred to herein as inlet halves "A" and "B", respectively.

As the average resistance of conduit 12 decreases, the voltage at point 18, i.e., the voltage applied to the positive input of differential amplifier 28, also decreases. Sensing a difference in voltage between its inputs, differential amplifier 28 provides an output signal which further biases the base of transistor 32, which in turns further biases the base of transistor 14. The resulting increase in bias to the base of transistor 14 results in a greater voltage being transmitted through transistor 14 and onto the divider network made up of resister 16 and the average resistance of conduit 12.

As more voltage is applied to point 18, the current through conduit 12 will increase resulting in a heating of conduit 12. The increase in temperature in conduit 12 will also result in an increase in the average resistance of conduit 12, which in turn results in an increase in the voltage applied to the positive input of differential amplifier 28. Such increase in voltage will continue until the difference in voltage at the inputs of differential amplifier 28 approaches zero.

It will also be noted that as the voltage applied to point 18 increases, the voltage applied to resistor 34 also increases. Consequently, the change in the average resistance of conduit 12 will be the primary factor effecting a change in the difference in voltages applied to the inputs of differential amplifier 28.

As fluid flow increases through conduit 12, the difference in voltage between points 20 and 22 also increases, however, since the voltage applied at point 18 serves to maintain the average resistance of conduit 12 relatively constant, saturation does not occur for a fairly wide dynamic range of operation. It has been found that the sensor shown in FIG. 1 is useful to at least 5,000 mL per minute.

An alternative embodiment of the sensor shown in FIG. 1 is depicted in FIG. 3. This alternative embodiment, generally designated 40, differs from sensor 10 in that instead of modifying the voltage applied to point 18 in order to maintain the average resistance of conduit 12 at a constant value, the voltage at point 18 is maintained constant. Since the average resistance of conduit 12 will now be allowed to change, this characteristic is compensated by compensator 42.

Before describing compensator 42, it will be noted that the voltage at point 18 is maintained at a constant value by connecting the negative input to differential amplifier 28 to a voltage reference ($V_{ref}$). As will be appreciated, the output of differential amplifier 28 will serve to bias transistor 32, and thus the base of transistor 14, until the voltage applied to the positive input of differential 28 approaches or equals $V_{ref}$.

Compensator 42, as previously indicated, accounts for the cooling, i.e., change in the average resistance, of conduit 12 as fluid passes therethrough. Compensator 42 is shown to include a current sensing resistor 44 which senses the current flowing to point 18. A signal representative of the current flowing through resister 44 is generated by amplifier 46. An analog multiplier 48 multiplies the sensed current signal with the output of differential amplifier 24. The output ($V_{out}$) of analog multiplier 48 is proportional to the mass-flow of fluid through conduit 12.

Consider the sensor shown in FIG. 3 in operation. As fluid flows through conduit 12, the average resistance value of conduit 12 will decrease. As average resistance decreases, voltage at point 18, i.e. between point 18 and ground, will also decrease resulting in a difference in voltage between the inputs of differential amplifier 28. The output of differential amplifier 28 in such a situation will provide a greater bias to the base of transistor 32, and thus to the base of transistor 14. The increase in biasing to the base of transistor 14 results in a greater voltage being applied to point 18, i.e. although average resistance is decreasing the voltage at point 18 remains substantially constant. As the bias to the base of transistor 14 increases to maintain the voltage at point 18 substantially constant, the current through resister 44 will also increase. As the current through resister 44 increases, the amount of compensation applied by multiplier 48 will also increase. Thus, as mass-flow of fluid through conduit 12 increases, the output of multiplier 48 also increases in proportion thereto and thus avoiding output signal saturation.

In a still further embodiment of the present invention, shown in FIG. 4, conduit 12 is flattened and designated as 50. It has been discovered that flattened conduit 50 has the effect of increasing the dynamic range of the sensor, i.e., increasing the point at which saturation occurs. Dynamic range has been found to increase over prior devices by six to seven times in the embodiment shown in FIG. 3 without the need for compensator 42. The effect of flattened conduit 50 when used in the preferred embodiment or in the embodiment shown in FIG. 3 with compensator 42 is to considerably extend the liner part of the dynamic range. In the preferred embodiment, the internal diameter of conduit 12 is approximately 0.016 inches. When flattened to a shape shown in FIG. 4, it is preferred that the internal spacing of conduit 50 be approximately 0.002 inches. It will be noted generally that as the tube 50 becomes thinner, the point at which saturation occurs becomes greater.

It will also be noted that for high pressure operation, it is preferred that all electrical connections to conduit 12 be braised. It will further be noted that it is preferred that fluid passed through conduit 12 be pre-heated to some generally uniform temperature. In one embodiment were gas is passed through conduit 12, the gas is pre-heated to a temperature of approximately 75° C. It will also be noted that in order to prevent ambient temperature from effecting sensor operation, it is preferred that conduit 12 be attached to a thermally conductive block which is maintained at a relatively constant temperature. In such an embodiment, conduit 12 is electrically isolated from the block by means of an insulating material such as approximately one-half inch of CERA-BLANKET sold by Manville of Denver, Colo.

As used in this application, the term resistive material shall mean a material having an electrical resistivity property and a thermal coefficient related to such electrical resistivity property. It will be noted that the higher the resistivity of the material from which conduit 12 is formed, the more sensitive is the sensor. The lower the resistivity of the material, the greater effect ambient temperature can have on the sensor.

While the invention has been described and illustrated with reference to specific embodiments, those skilled in the art will recognize that modification and variations may be made without departing from the principles of the invention as described herein above and set forth in the following claims.

What is claimed is:

1. Apparatus for sensing the mass flow of a fluid and for generating an output signal representative of the sensed mass flow, comprising:

a conduit, for the passage of said fluid therethrough, said conduit formed from resistive material;

a voltage source, connected to a first point on said conduit, for providing a voltage to said first point in response to a control signal;

a differential amplifier having at least two inputs for generating said output signal, wherein said output signal is representative of the difference in voltage between said two inputs, wherein one of said inputs is connected to a second point on said conduit, and wherein the other of said inputs is connected to a third point on said conduit, said second point being spaced up stream from said third point; and control means, connected to said voltage source, for generating said control signal so that the voltage provided to said first point is controlled in relation to the flow of fluid through said conduit.

2. The apparatus of claim 1, wherein said resistive material comprises approximately 50.5% nickel, 0.01% carbon, 0.3% manganese, 0.2% silicon and 48.99% iron.

3. The apparatus of claim 1, wherein said first point is the mid-point of said conduit.

4. The apparatus of claim 1, wherein said first point is between said second and third points.

5. The apparatus of claim 4, wherein said second and third points are spaced equidistant from said first point.

6. The apparatus of claim 1, wherein said voltage source comprises a transistor connected to a supply voltage, wherein said control signal is applied to the base of said transistor so that more or less voltage is transmitted through said transistor in response to said control signal.

7. The apparatus of claim 1, wherein said conduit has an equivalent resistance value, and wherein said control means generates said control signal so that the voltage applied to said first point is regulated to maintain the equivalent resistance of said conduit at a desired value.

8. The apparatus of claim 7, wherein said desired value is a constant value.

9. The apparatus of claim 8, wherein said control means comprises:

a second differential amplifier having at least two inputs for generating a difference signal reflective of the difference in voltage between said two inputs, wherein one of said inputs is connected to said first point, and wherein the other of said inputs is connected to a reference voltage, wherein said difference signal is utilized as said control signal.

10. The apparatus of claim 9, wherein said reference voltage is proportional to the voltage applied to said first point.

11. The apparatus of claim 1, wherein said control means generates said control signal so that the voltage applied to said first point is maintained at a desired value.

12. The apparatus of claim 11, further comprising compensation means for compensating said output signal to account for the cooling of said conduit as said fluid passes therethrough.

13. The apparatus of claim 12, wherein said compensation means comprises current sensing means for sensing the current flowing to said first point and generating a current signal representative of the sensed current, and a multiplier for multiplying the output of said differential amplifier and said current signal and for generating an output signal representative of said multiplication.

14. The apparatus of claim 1, wherein said conduit comprises a flattened shape.

15. The apparatus of claim 1, wherein said resistive material has a high electrical resistivity around 430 microhms-mm.

16. The apparatus of claim 2, wherein said resistive material has a high temperature coefficient of resistance of around 0.0029 per degree Centigrade.

17. A method for sensing the mass flow of a fluid and for generating an output signal representative of the sensed mass flow, comprising the steps of:

passing said fluid through a conduit, said conduit being formed from resistive material;

providing a voltage to a first point on said conduit in response to a control signal;

generating an output signal, wherein said output signal is representative of the difference in voltage between a second point on said conduit and a third point on said conduit, said second point being spaced up stream from said third point; and generating said control signal so that the voltage provided to said first point is controlled in relation to the flow of fluid through said conduit.

18. The apparatus of claim 15, wherein said resistive material comprises approximately 50.5% nickel, 0.01% carbon, 0.3% manganese, 0.2% silicon and 48.99% iron.

19. The method of claim 17, wherein said conduit has an equivalent resistance value, and wherein said step of generating said control signal comprises generating said control signal so that the voltage applied to said first point is regulated to maintain the equivalent resistance of said conduit at a desired value.

20. The method of claim 19, wherein said desired value is a constant value.

21. The method of claim 17, wherein said step of generating said control signal comprises generating said control signal so that the voltage applied to said first point is maintained at a desired value.

22. The method of claim 21, further comprising the step of compensating said output signal to account for the cooling of said conduit as said fluid passes therethrough.

23. The method of claim 22, wherein said step of compensating said output signal comprises the steps of sensing the current flowing to said first point and generating a current signal representative of the sensed current, multiplying said output signal by said current signal and generating a second output signal representative of said multiplication.

24. The method of calim 17, wherein said conduit comprises a flattened shape.

* * * * *